(12) United States Patent
Tan et al.

(10) Patent No.: US 9,017,718 B2
(45) Date of Patent: Apr. 28, 2015

(54) DUAL AND SINGLE LAYER DOSAGE FORMS

(75) Inventors: Hock Seng Tan, East Brunswick, NJ (US); Siew Lian Chung, East Brunswick, NJ (US)

(73) Assignee: Bionex Pharmaceuticals LLC, North Brunswick, NJ (US)

( * ) Notice: Subject to any disclaimer, the term of this patent is extended or adjusted under 35 U.S.C. 154(b) by 74 days.

(21) Appl. No.: 13/060,325

(22) PCT Filed: Apr. 22, 2010

(86) PCT No.: PCT/US2010/031991
§ 371 (c)(1),
(2), (4) Date: Feb. 23, 2011

(87) PCT Pub. No.: WO2010/135053
PCT Pub. Date: Nov. 25, 2010

(65) Prior Publication Data
US 2011/0280925 A1    Nov. 17, 2011

Related U.S. Application Data

(60) Provisional application No. 61/216,792, filed on May 21, 2009.

(51) Int. Cl.
| A61M 35/00 | (2006.01) |
| A61K 47/32 | (2006.01) |
| A61K 47/34 | (2006.01) |
| A61K 9/00  | (2006.01) |
| A61K 9/70  | (2006.01) |

(52) U.S. Cl.
CPC .............. *A61M 35/00* (2013.01); *A61K 9/0056* (2013.01); *A61K 9/006* (2013.01); *A61K 9/7007* (2013.01); *A61K 47/32* (2013.01); *A61K 47/34* (2013.01)

(58) Field of Classification Search
None
See application file for complete search history.

(56) References Cited

U.S. PATENT DOCUMENTS

| 6,791,003 | B1 * | 9/2004 | Choi et al. ............ 602/48 |
| 2003/0044446 | A1 * | 3/2003 | Moro et al. ............ 424/426 |
| 2004/0208931 | A1 * | 10/2004 | Friend et al. ............ 424/471 |
| 2006/0198873 | A1 * | 9/2006 | Chan et al. ............ 424/443 |
| 2007/0122456 | A1 * | 5/2007 | Lindberg ............ 424/439 |
| 2008/0166404 | A1 * | 7/2008 | Tzannis et al. ............ 424/451 |
| 2009/0196908 | A1 * | 8/2009 | Lee et al. ............ 424/443 |

OTHER PUBLICATIONS

Duram™ 204 Mono- and D8glyceride Emulsifier; Product Data Sheet; IOI Group; Loders Croklaan; Channahon, Illinois; Jun. 27, 2006, 1 page.

* cited by examiner

*Primary Examiner* — Susan Tran
*Assistant Examiner* — Jessica Worsham
(74) *Attorney, Agent, or Firm* — Moser Taboada

(57) ABSTRACT

Provided is a dual-release, dual-adhesiveness flexible thin film dosage form comprising: a quick-release subfilm comprising an admixture of polymer, which comprises predominantly highly water-soluble polymer(s), and a bioactive agent, the polymers and other components of the quick-release subfilm adapted to provide 20 minutes or less erodibility for the quick-release subfilm; and laminated against the quick-release subfilm, a sustained-release subfilm comprising an admixture of polymer, which comprises predominantly hydrophilic, bioadhesive polymer(s), and a second bioactive agent, which can be the same as the first, the polymers and other components of the sustained-release subfilm adapted to provide erodibility of 1 hour or more and 20 hours or less for the sustained-release subfilm, the dosage form having a thickness of 30 mil or less, and being more adhesive on the sustained-release side.

18 Claims, 1 Drawing Sheet

DUAL AND SINGLE LAYER DOSAGE FORMS

This application claims priority to PCT patent application Ser. No. PCT/US10/31991, filed 22 Apr. 2010, which claims the priority of U.S. Application No. 61/216,792, filed 21 May 2009.

Embodiments of the present invention generally relate to a convenient dosage form adapted to be applied to mucosal tissue and provide a rapid release of a bioactive agent, and a sustained release.

Mucoadhesive films, also referred to as orally dissolving or eroding thin films or oral bioadhesive films, have emerged as advanced dosage forms that provide a useful alternative to traditional tablets, capsules, soft gels and liquids. Similar in size, shape and thickness to a postage stamp, these thin film strips, squares or discs containing active pharmaceutical ingredient (API) are typically designed for intra-oral administration, with the patient placing the strip on or under the tongue (lingual or sublingual) or along the inside of the cheek (buccal). As the thin film dissolves/erodes, drug is released and delivered to the blood stream either intragastrically, buccally or sublingually.

Mucoadhesive films can generally be classified into two categories: fast dissolving films and slow dissolving/eroding films. Fast dissolving films, which typically comprise polymers of high water solubility, are designed as a convenient form for lingual administration and gastro-intestinal (GI) tract absorption. The active ingredients are incorporated in the film matrix, which dissolves rapidly on the tongue and is then swallowed into the GI tract for absorption. No water is required, making this dosage form convenient for the consumer or patient. This type of dosage form is particularly useful for pediatric and geriatric patients, and patients with difficulty in swallowing tablets. Indeed, it is known in the art to use such films for administering breath freshening agents such as menthol. The first commercial non-drug product in the United States to use thin film for oral hygiene purposes was the Listerine PocketPaks breath-freshener strip. Since then, thin film products for other breath fresheners, as well as a number of cold, cough, flu and anti-snoring medications, have entered the marketplace in the United States, Europe and Japan.

Known films for administering breath freshening agents and active pharmaceutical agents (API) are generally comprised of a water-soluble polymer suitable for human consumption and a compound that enhances the flexibility and wettability of the film, typically selected from polyols, surfactants and other plasticizers. For example, U.S. Pat. No. 5,948,430 describes a monolayer film which can be adhered to the oral cavity to release a pharmaceutically active ingredient, wherein the film comprises water-soluble polymer, a polyalcohol, a surfactant and a plasticizer, a pharmaceutically active ingredient, and a flavoring agent. U.S. Pat. No. 7,132,113 describes a rapidly disintegrating flavored film (breath freshening film) that quickly and completely disintegrates upon contact with mucosal tissue in the oral cavity of a human; the film incorporates a hydroxypropyl cellulose, a modified starch and a flavor ingredient.

The second class of bioadhesive films is designed for controlled or sustained release of API. These films contain at least a slow dissolving or eroding polymer. U.S. Pat. No. 4,713,243 describes an extruded thin film, useful in intra-oral controlled-releasing delivery, having a water soluble or swellable polymer matrix bioadhesive layer which can adhere to a wet mucous surface and which bioadhesive layer consists of a hydroxypropyl cellulose, a homopolymer of ethylene oxide, a water-insoluble polymer such as ethyl cellulose, propyl cellulose, polyethylene, polypropylene or the like, and a plasticizer.

Slow dissolving films are mainly designed for systemic administration via the interior lining of the cheek (buccal mucosa) or for local treatment. Somewhat analogous to thin films are dissolving buccal tablets. There are a few commercial buccal tablet products in development, but no marketed buccal films to date, though many research and development activities have been reported. One possible reason for the unpopularity of the buccal (applied to the inner cheeks) products is that patients find the products obtrusive and uncomfortable, particularly when so placed over an extended period of time. Also, patients who suffer from dry mouth conditions may find buccal tablets irritating and refuse to use this dosage form.

Thin film intra-oral drug delivery technology offers a number of potential advantages over other dosage forms, such as ingestible tablets, chewable tablets, orally dissolving tablets, soft gels, liquids or inhalants including:

(1) The potential to improve the onset of action, lower the dosing, and enhance the efficacy and safety profile of the medicament. Conversely, all tablet dosage forms, soft gels and liquid formulations primarily enter the blood stream via the gastrointestinal tract, which subjects the drug to degradation from stomach acid, bile, digestive enzymes and other first pass effects. As a result, such formulations often require higher doses and generally have a delayed onset of action. Buccal and sublingual thin film drug delivery can avoid these issues and yield quicker onsets of action at lower doses;

(2) Improved dosing accuracy relative to liquid formulations since every strip is manufactured to contain a precise amount of the drug;

(3) More accurate administration of drugs as well as improved compliance due to the intuitive nature of the dosage form and its inherent ease of administration. These properties are especially beneficial for pediatric, geriatric and neurodegenerative disease patients where proper and complete dosing can be difficult; and (4) Rapid dissolution without the need for water provides an alternative to patients with swallowing disorders and to patients suffering from nausea, such as those patients receiving chemotherapy.

In certain embodiments, the present invention combines the advantages of both fast dissolving films and slow eroding films with a bilayer film construct. The construct can provide for ease of application. In certain embodiments, the invention provides a single-layer film that, with a class of bioactive agents, provides sustained release in a single layer. Another innovation provided by the present invention is the method of administration. In certain embodiments, the dosage form is applied to the tongue and adheres to the palate, for instance as the subject closes his or her mouth. The palate is flat and is able to accommodate a larger dosage form. The film is designed such that it disintegrates and dissolves upon administration and the drug is released for oral and/or transmucosal absorption. In addition, the invention provides a method to alleviate or eliminate undesired taste or sensation of drugs or API, in the oral thin film.

SUMMARY

Embodiments of the present invention generally relate to methods for subcutaneously delivering a sided, planar microchip and devices for effecting such delivery.

Provided, among other things, is a dual-release, dual-adhesiveness flexible thin film dosage form comprising: a quick-release subfilm comprising an admixture of polymer, which comprises predominantly highly water-soluble polymer(s), and a bioactive agent, the polymers and other components of the quick-release subfilm adapted to provide 20 minute or less erodibility for the quick-release subfilm; and laminated against the quick-release subfilm, a sustained-release subfilm comprising an admixture of polymer, which comprises predominantly hydrophilic, bioadhesive polymer(s), and a second bioactive agent, which can be the same as the first, the polymers and other components of the sustained-release subfilm adapted to provide erodibility of 1 hours or more and 20 hours or less for the sustained-release subfilm, the dosage form having a thickness of 30 mil or less, and being more adhesive on the sustained-release side.

Also provided, among other things, is a flexible thin film dosage form consisting of a sustained-release film which comprises: a admixture of polymer, which comprises predominantly hydrophilic, bioadhesive polymer(s), and a bioactive agent, which can be the same as the first, the polymers and other components of the sustained-release subfilm adapted to provide a bioactive release period of 1.5 hours or more and 15 hours or less, wherein the dosage form having a thickness of 30 mil or less, wherein the bioactive agent having a titratable amine and (a) two or more aromatic ring or (b) one or more aromatic rings that (i) incorporate nitrogen, and/or (ii) are directly substituted with N or O of substituent groups, and wherein a predominant amount of the predominantly hydrophilic bioadhesive polymer(s) comprises crosslinked polymers of acrylic acid.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

Results of dissolution (drug release) in a monolayer film are presented in FIG. 1.

Figure 2:
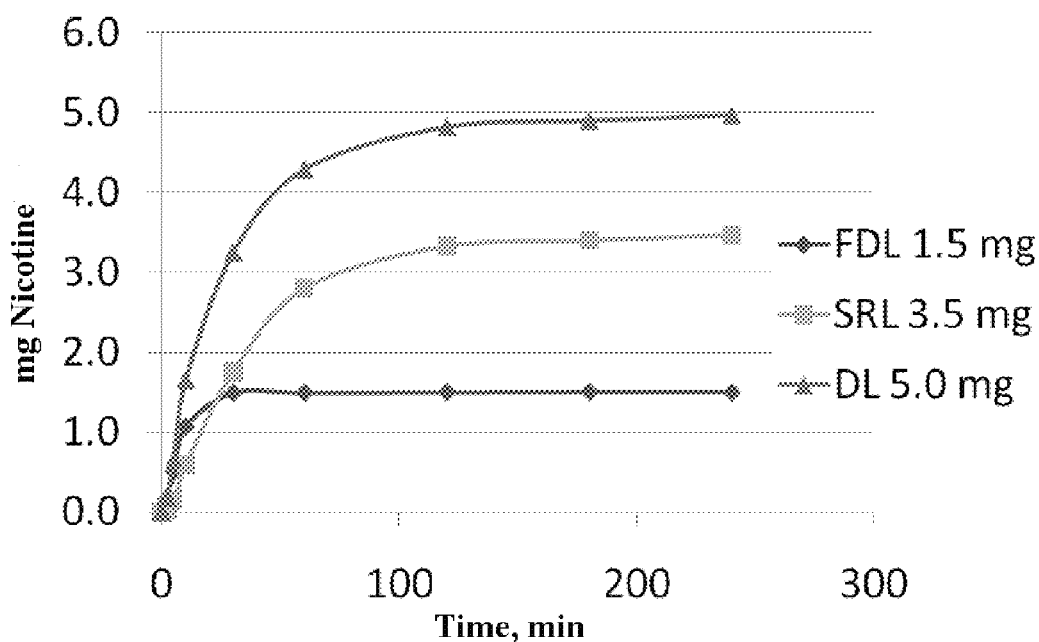

Results of dissolution (drug release) in a bilayer film are presented in FIG. 2. The results show that the bilayer film releases the drug, nicotine, in the sustained manner sought. That is, in the bilayer film, the FDL component rapidly released 1.5 mg of nicotine in about 15 min, and the SRL component released the nicotine slowly for period of up to about 150 min.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

A "bioactive agent" is a substance such as a chemical that can act on a cell, virus, organ or organism, including but not limited to drugs (i.e. pharmaceuticals) to create a change in the functioning of the cell, virus, organ or organism. In certain embodiments of the invention, bioactive agents are organic molecules having molecular weight of about 600 or less. A bioactive agent can be a medicament, i.e. a substance used in therapy of an animal, preferably a human.

The "bioactive agent release period" is the amount of time it takes for a dosage form or a subfilm thereof to release 85% of its bioactive agent (in a USP phosphate buffer solution, pH 6.8 with stirring). For the minimum/maximum release periods recited for the sustained-release subfilm, the period is measured with the dosage form or sustained-release subfilm adhered on a non-eroding substrate (such as a glass slide).

To treat the indications with the dosage form of the invention, an "effective amount" of a bioactive agent will be recognized by clinicians but includes an amount effective to treat, reduce, alleviate, ameliorate, eliminate or prevent one or more symptoms of the disease sought to be treated or the condition sought to be avoided or treated, or to otherwise produce a clinically recognizable favorable change in the pathology of the disease or condition. Bioactive agents can be presented in the dosage form in effective amounts, or in a number of the dosage forms applied at about the same time in amounts that total effective amounts.

The term "erodibility," as used with respect to the quick-release subfilm refers to the amount of time it takes for that subfilm of the dosage form (quick-release or sustained-release) to more than 85% disappear in a USP phosphate buffer solution, pH 6.8 with stirring. As used with respect to the sustained-release subfilm, the term refers to the amount of time it takes for that subfilm of the dosage form, adhered on a non-eroding substrate (such as a glass slide), to more than 80% disappear in a USP phosphate buffer solution, pH 6.8 with stirring.

The expression "highly water-soluble polymer(s)" is defined by the polymer's functional role in helping provide the erodibilities recited in conjunction with this expression. The degree of water solubility is defined by the degree needed to provide the recited erodibility in the context of the other components of the relevant subfilm.

The term "laminated" refers to two films be stably annealed together, without any implication as to the method by with that bond was formed.

The expression "predominantly hydrophilic polymer(s)" is defined by the polymer's functional role in helping provide the erodibilities recited in conjunction with this expression. The degree of hydrophilicity is defined by the degree needed to provide the recited erodibility in the context of the other components of the relevant subfilm. More generally, the expression denotes that the polymers are wetted when exposed to water, but do not readily dissolve.

"Treatment" means the management and care of a patient for the purpose of combating a disease, disorder or condition. The term is intended to include the delaying of the progression of the disease, disorder or condition, the alleviation, amelioration or relief of symptoms and complications, and/or the cure or elimination of the disease, disorder or condition. The animal to be treated can be a mammal, in particular a human being.

The films or subfilms of the dosage form will generally contain, polymers, bioactive agent(s), taste modifiers, plasticizers and or release modifiers, buffering agents, preservatives, and the like. The two subfilms differ in erodibility based substantially on the types of polymers comprising the subfilms, but this does not absolutely imply that say the quick-release subfilm does not have any predominantly hydrophilic, bioadhesive polymers. Instead, any predominantly hydrophilic, bioadhesive polymer is present in an amount which, given the amount of highly water-soluble polymer present allows for fast erodibility. Similarly, any highly water-soluble polymer present in the sustained-release film or subfilm is in an amount which, given the amount of predominantly hydrophilic, bioadhesive polymer present allows for relatively slower erodibility.

For example, in the sustained-release film or subfilm, such components can be present in amounts such as outlined below:

| Ingredient Class | Wt. % Range |
|---|---|
| Bioactive | 10-35 |
| Predominantly hydrophilic, bioadhesive polymer | 15-40 |
| Highly water-soluble polymer | 0-25 |
| Plasticizer | 15-40 |
| Taster modifier | 3-10 or 12 |

In any film or subfilm, the bioactive can in certain embodiments be present in an amount of 10% or more, 11% or more, 12% or more, 13% or more, 14% or more, 15% or more, 16% or more, 17% or more, 18% or more, 19% or more, 20% or more; or 35% or less, 34% or less, 33% or less, 32% or less, 31% or less, 30% or less, 29% or less, 28% or less, 27% or less, 26% or less, 25% or less, 24% or less, 23% or less, 22% or less, 21% or less, 20% or less, 19% or less, 18% or less, 17% or less, 16% or less, or 15% or less. The plasticizer can in certain embodiments be present in an amount of 5% or more, 10% or more, 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more; or 40% or less, 39% or less, 38% or less, 37% or less, 36% or less, 35% or less, 34% or less, 33% or less, 32% or less, 31% or less, or 30% or less. (Unless otherwise specified, the amounts or percentages in this specification are wt/wt amounts or percentages.)

In the sustained-release film or subfilm, the predominantly hydrophilic, bioadhesive polymer can in certain embodiments be present in an amount of 15% or more, 16% or more, 17% or more, 18% or more, 19% or more, 20% or more, 21% or more, 22% or more, 23% or more, 24% or more, 25% or more, 26% or more, 27% or more, 28% or more, 29% or more, 30% or more; or 40% or less, 39% or less, 38% or less, 37% or less, 36% or less, 35% or less, 34% or less, 33% or less, 32% or less, 31% or less, 30% or less, 29% or less, 28% or less, 27% or less, 26% or less, or 25% or less. The highly water-soluble polymer can in certain embodiments be present in an amount of 0% or more, 1% or more, 2% or more, 3% or more, 4% or more, 5% or more, 6% or more, 7% or more, 8% or more, 9% or more, 10% or more, 11% or more, 12% or more, 13% or more, 14% or more, 15% or more; or 25% or less, 24% or less, 23% or less, 22% or less, 21% or less, 20% or less, 19% or less, 18% or less, 17% or less, 16% or less, or 15% or less.

For example, in the quick-release subfilm, such components can be present in amounts such as outlined below:

| Ingredient Class | Wt. % Range |
|---|---|
| Bioactive | 10-30 or 35 |
| Predominantly hydrophilic, bioadhesive polymer | 0-10 |
| Highly water-soluble polymer | 50-85 |
| Plasticizer/release modifier | 5 or 10 or 15-40 |
| Taster modifier | 0 or 3-10 or 12 |

In this quick-release subfilm, the predominantly hydrophilic, bioadhesive polymer can in certain embodiments be present in an amount of 0% or more, 1% or more, 2% or more, 3% or more, 4% or more, 5% or more, 6% or more, 7% or more, 8% or more, or 9% or more; or 10% or less, 9% or less, 8% or less, 7% or less, 36% or less, 5% or less, 4% or less, 3% or less, 2% or less, or 1% or less. The highly water-soluble polymer can in certain embodiments be present in an amount of 50% or more, 51% or more, 52% or more, 53% or more, 54% or more, 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more; or 85% or less, 84% or less, 83% or less, 82% or less, 81% or less, 70% or less, 79% or less, 78% or less, 77% or less, 76% or less, 75% or less, 74% or less, 73% or less, 72% or less, 71% or less, 70% or less, 69% or less, 68% or less, 67% or less, 66% or less, or 65% or less.

In certain embodiments, the amounts in any film or subfilm are: bioactive: 5-20%; predominantly hydrophilic, bioadhesive polymer: 10-40%; highly water-soluble polymer: 5-30%; plasticizer/release agent: 5-10%; taste modifier: 5-10%; buffering agents: as needed or 1-2%.

Some examples of highly water-soluble polymers are appropriate cellulose derivatives (e.g., hydroxypropyl methyl-cellulose), polyvinylpyrrolidone, polyvinyl alcohol, polyethylene oxide, and polyvinyl alcohol grafted polyethylene glycol copolymer (Kollicoat® IR, BASF), or mixtures thereof. For example, polyvinyl alcohol grafted polyethylene glycol copolymer and polyethylene oxide (e.g., PolyOx™ N-10) impart fast-dissolution and provide for ease in formulation. Kollicoat® IR is a polyvinyl alcohol-polyethylene glycol graft copolymer of about 45,000 daltons (by gel permeation chromatography). Appropriate polyethylene oxides for this purpose generally have average MW equal to or greater than 50,000 and equal to or less than 500,000. For example, PolyOx™ WSR N-10 (Dow), a polyethylene oxide with MW 100,000, can be used.

Some examples of predominantly hydrophilic, bioadhesive polymers are a number of bioadhesives: a) natural polymers, b) modified natural polymers, and c) synthetic polymers. For example, predominantly hydrophilic, bioadhesive polymers can be xanthan gum, carrageenan, pectin, sodium carboxymethylcellulose, alginate, polyacrylic acids, high molecular weight polyethylene oxide, or mixtures thereof. In some embodiments, predominantly hydrophilic, bioadhesive polymers comprise polyacrylic acids, high molecular weight polyethylene oxide, or mixtures thereof. Such polyacrylic acids include, for example, Carbopol, Polycarbophil polyacrylic acids.

Carbopols are polymers of acrylic acid cross-linked with polyalkenyl ethers or divinyl glycol. For example, Carbopol 971 is high molecular weight polymer of acrylic acid crosslinked with allyl ethers of pentaerythritol, with equivalent weight 76±4, and Brookfield RVT Viscosity of 4000-11000 cP (0.5 wt % mucilage at pH 7.5, 20 rpm at 25° C.) Carbopol 974 differs in having a Brookfield RVT Viscosity of 29,400-39,400 cP. Carbopol 1342 is a high molecular weight copolymer of acrylic acid and a long chain alkyl methacrylate crosslinked with allyl ethers of pentaerythritol, with a Brookfield RVT Viscosity of 9,500-26,500 cP. This last example illustrates that a poly acrylic acid can include some polymerization-compatible monomers that are not acrylic acid. Where such added monomers reduce adhesiveness, the polymer can be avoided or blended with more adhesive polymers, as appropriate. Appropriate polyethylene oxides for this purpose generally have average MW equal to or greater than 2,000,000. For example, PolyOx™ WSR-301, a polyethylene oxide with MW 4,000,000, can be used.

Crosslinked polymers of acrylic acid are adhesive polymer of predominantly acrylic acid that are adhesive.

The films or subfilms can, in certain embodiments, have additional polymers. The sustained-release subfilm for example can contain water-insoluble polymers such as ethyl cellulose, propyl cellulose, polyethylene, polypropylene or the like.

Additional details on polymers mentioned above can be found in Handbook of Pharmaceutical Excipients (Rowe et al., 2003, Handbook of Pharmaceutical Excipients. 4th Ed. Pharmaceutical Press, London).

Appropriate plasticizers will be recognized by those of skill in the art, and include, for example, propylene glycol, glycerin, PEG-4000, PEG-400, and the like. The plasticizer can have surfactant properties, such that it can act as a release modifier. For example, non-ionic detergents such at Brij 58 (polyoxyethylene (20) cetyl ether), and the like, can be used. Plasticizers impart flexibility to the dosage forms, and can affect the release profile for bioactive agent.

Taste modifiers such as flavors, sweeteners, and taste masking agents can be incorporated in the dosage form to provide a pleasant taste and mouth-feel when the dosage form is administered in the oral cavity. Taste modifiers include, for example, flavoring agents (such as peppermint oil, other flavored oils, Cocoa powder, and the like), sweeteners (such as sodium saccharin, glucose, fructose, Aspartame, Sucralose, Steviosides, and the like), taste modifiers (such as Cremophor® RH-40 (polyoxy 40 hydrogenated castor oil, BASF), Clove oil, diglycerides), taste masking agents (such as Magnasweet 100 (mono-ammonium glycyrrhizinate, Mafco, Inc.), Eudragit E-100 (2-dimethylamino)ethyl methacrylate polymer, Evonik)), and the like. Additional examples include: the essential oils or water soluble extracts of menthol, wintergreen, peppermint, sweet mint, spearmint, vanillin, cherry, chocolate, cinnamon, clove, lemon, orange, raspberry, rose, spice, violet, herbal, fruit, strawberry, grape, pineapple, peach, kiwi, papaya, mango, coconut, apple, coffee, plum, watermelon, nuts, durian, green tea, grapefruit, banana, butter or chamomile; sugar; dextrose; lactose; mannitol; sucrose; xylitol; malitol; acesulfame potassium; talin; glycyrrhizin; sucralose; aspartame; saccharin; sodium saccharin; sodium cyclamate and honey.

The films can be stand-alone or self-supporting, meaning the films have enough integrity so that there is no need to support them with additional backings, such as non-dissolvable films, such as polyethylene films Also, preservatives or stabilizers can be added when needed. Preservatives can include anti-microbial agents and non-organic compounds, and are exemplified by sodium benzoate, parabens and derivatives, sorbic acid and salts, propionic acids and salts, sulfur dioxide and sulfites, acetic acid and acetates, nitrites and nitrates, and the like.

The dosage form (single or dual layer) can for example be square, rectangular, circular, oval, or any number of shapes. Square dosage forms can be for example 1-4 cm on the side. Circular (disk) dosage forms can be for example 1-2 cm in diameter. The dosage form (single or dual layer) is typically 30 mil (0.762 mm) or less in thickness. In some embodiments, the dosage form (single or dual layer) is 29 mil or less, or 28 mil or less, 27 mil or less, 26 mil or less, 25 mil or less, 24 mil or less, 23 mil or less, 22 mil or less, 21 mil or less, 20 mil (0.508 mm) or less, 19 mil or less or 18 mil or less, 17 mil or less, 16 mil or less, 15 mil or less, 14 mil or less, 13 mil or less, 12 mil or less, 11 mil or less, 10 mil (0.254 mm) or less, 9 mil or less or 8 mil or less in thickness. In some embodiments, the dosage form (single or dual layer) is 1 mil or more, 2 mil or more, 3 mil or more, 4 mil or more, or 5 mil or more, 6 mil or more, 7 mil or more, 8 mil or more, 9 mil or more, 10 mil or more, 11 mil or more, 12 mil or more, 13 mil or more, 14 mil or more, or 15 mil or more 16 mil or more, 17 mil or more, 18 mil or more, 19 mil or more, or 20 mil or more in thickness. In certain embodiments, the dosage form area (e.g., length× width, single or dual layer) is 20 $cm^2$ or less, 19 $cm^2$ or less, 18 $cm^2$ or less, 17 $cm^2$ or less, 16 $cm^2$ or less, 15 $cm^2$ or less, 14 $cm^2$ or less, 13 $cm^2$ or less, 12 $cm^2$ or less, 11 $cm^2$ or less, 10 $cm^2$ or less, 9 $cm^2$ or less, 8 $cm^2$ or less, 7 $cm^2$ or less, 6 $cm^2$ or less, 5 $cm^2$ or less, 4 $cm^2$ or less, 3 $cm^2$ or less or 2 $cm^2$ or less. In certain embodiments, the dosage form area (single or dual layer) is 1 $cm^2$ or more, 2 $cm^2$ or more, 3 $cm^2$ or more, 4 $cm^2$ or more or 5 $cm^2$ or more. In certain embodiments, the dosage form weight (single dosage form, single or dual layer) is 200 mg or less, 190 mg or less, 180 mg or less, 170 mg or less, 160 mg or less, 150 mg or less, 140 mg or less, 130 mg or less, 120 mg or less, 110 mg or less, 100 mg or less, 90 mg or less, 80 mg or less, 70 mg or less, 60 mg or less, 50 mg or less, 40 mg or less or 30 mg or less. In certain embodiments, the dosage form weight (single or dual layer) is 20 mg or more, 30 mg or more, 40 mg or more, 50 mg or more or 60 mg or more.

The quick-release subfilm can be, for example, 20 mil (0.508 mm) or less, 19 mil or less or 18 mil or less, 17 mil or less, 16 mil or less, 15 mil or less, 14 mil or less, 13 mil or less, 12 mil or less, 11 mil or less, 10 mil (0.254 mm) or less, 9 mil or less or 8 mil or less in thickness. In some embodiments, the quick-release subfilm is 0.5 mil or more, 1 mil or more, 2 mil or more, 3 mil or more, or 4 mil or more in thickness. The sustained-release subfilm can be, for example, 20 mil (0.508 mm) or less, 19 mil or less or 18 mil or less, 17 mil or less, 16 mil or less, 15 mil or less, 14 mil or less, 13 mil or less, 12 mil or less, 11 mil or less, 10 mil (0.254 mm) or less, 9 mil or less or 8 mil or less in thickness. In some embodiments, the sustained-release subfilm is 0.5 mil or more, 1 mil or more, 2 mil or more, 3 mil or more, or 4 mil or more in thickness.

For bioactive agents needing higher dosages, more than one dosage form can be used at each administration, such as 1-4 dosage forms per administration. Dosages of bioactive agent may be for example from 0.01 mg per administration to 100 mg per administration. Administrations can be repeated as appropriate for the bioactive agent, and the release profile provided by preceding administrations.

In certain embodiments, the dosage form exhibits one or more of the following characteristics:
  sufficient flexibility to adapt to the surface of the mucosal tissue to which it is adapted to be administered;
  comfortable and unobtrusive during use;
  easy to administer to the site of application;
  remains in place on the mucosal tissue without moving once administered;
  capable of providing a rapid release of active agent immediately subsequent to administration followed by a sustained release of the active for an extended period; and
  completely dissolves and/or erodes at the end of the release period without the need for the physical removal of any residue.

In certain embodiments, the polymers and other components of the quick-release subfilm are adapted to provide 20 minute or less erodibility for the quick-release subfilm. In certain embodiments, the polymers and other components of the quick-release subfilm are adapted to provide 15 minute or less, 10 minute or less, 9 minute or less, 8 minute or less, 7 minute or less, 6 minute or less or 5 minute or less erodibility for the quick-release subfilm. In certain embodiments, the polymers and other components of the quick-release subfilm are adapted to provide 10 minute or more, 8 minute or more, 7 minute or more, 6 minute or more, 5 minute or more, 4 minute or more, 3 minute or more, 2 minute or more or 1 minute or more erodibility for the quick-release subfilm.

In certain embodiments, the polymers and other components of the sustained-release film or subfilm are adapted to provide 20 hours or less erodibility for the sustained-release layer. In some embodiments, the polymers and other components of the sustained-release film or subfilm are adapted to provide 15 hours or less erodibility, 14 hours or less erodibility, 13 hours or less erodibility, 12 hours or less erodibility, 11 hours or less erodibility, 10 hours or less erodibility, 9 hours or less erodibility or 8 hours or less erodibility for the sustained-release layer. In some embodiments, the polymers and other components of the sustained-release film or subfilm are adapted to provide 1 hour or more erodibility, 1.5 hour or more erodibility, 2 hour or more erodibility, 3 hours or more erodibility or 4 hours or more erodibility for the sustained-release layer.

In certain embodiments, the polymers and other components of the sustained-release film or subfilm are adapted to provide a bioactive release period of 20 hours or less for the sustained-release layer. In some embodiments, the polymers and other components of the sustained-release film or subfilm are adapted to provide a bioactive release period of 15 hours or less, 14 hours or less, 13 hours or less, 12 hours or less, 11 hours or less, 10 hours or less, 9 hours or less, or 8 hours or less for the sustained-release layer. In some embodiments, the polymers and other components of the sustained-release film or subfilm are adapted to provide a bioactive release period of 1 hour or more, 1.5 hour or more, 2 hour or more, 3 hours or more, 4 hours or more, 5 hours or more, 6 hours or more, 7 hours or more, or 8 hours or more for the sustained-release layer.

In certain embodiments, bioactive is released and delivered to the blood stream via the gastrointestinal system or via mucosal tissue, or is released and delivered locally at or near the site to which the dosage form is adhered. Typically, where the dosage form is used in the mouth, any transmucosal delivery may be, for example, buccal, sublingual, via the palate, or the like. Particularly for bioactive from the sustained-release layer, it can be that some is delivered transmucosally at or near the site that the dosage form is adhered, and some is delivered via the gastrointestinal tract. Other mucosal tissue, such as rectal or vaginal tissue, can also be used as the site of application.

As will be recognized by those of skill in the art, a wide variety of bioactive agents can be delivered using the dosage form. These can include therapeutic agents, nutritional supplements and hygiene aids. The therapeutic agents are exemplified by analgesics, a-adrenergic receptor blockers, anti-Alzheimer's disease medication, antianginal, antianxiety, antiarrythmics, antiarthritics, antibiotics, anticoagulants, thrombolytics, anticonvulsants, anti-Parkinson medications, anti-depressants, anti-diabetics, anti-diarrheal, anti-epileptics, antifungal, anti-gout, anti-heartworm medication for dogs, antihistamines, antihypertensives, anti-inflammatories, anti-infectives, antimigraines, anti-nauseants/anti-emetics, antineoplastics/anti-tumor agents, anti-pruitics, antipsychotics, antipyretics, anti-spasmodics, antivirals, beta-blockers, bronchial dilators/anti-asthmatics, calcium antagonists, cardiac agents, cardiotonics, central nervous system actives, contraceptives, coronary vasodilators, cough/cold remedies, dietary supplements, including vitamins and minerals, diuretics, fertility agents, flea control agents for animals (e.g., Ivermectin), H 2 receptor antagonists, herbal actives, hormones, hypoglycemics, hypolipidemics, muscle relaxants, ovulation stimulators, peptide active agents, polypeptide active agents, proteins (such as insulin, calcitonin, LHRH and the like), sedatives, hypnotics, sexual dysfunction active agents, sleep aids, smoking cessation aids, steroids and steroidals, tranquilizers, laxatives, ophthalmic preparations, nutritional supplements, breath fresheners, breath deodorants, saliva substitutes, antigingivitis agents, anti-cavity agents, anti-plaque agents, diagnostic indicators, and local anesthetics. Also included for example are bioactive agents for treatment of osteoporosis, hormone replacement, treatment of periodontal disease, antiseptics, corticosteroids, non-steroidal anti-inflammatory agents, antiviral agents and vaccines.

Exemplary antihistamines include, for example, chlorpheniramine HCl, Exemplary antihypertensives include for example verapamil HCl. Exemplary vasodilators include for example papaverine HCl. Exemplary local anesthetics include for example procaine HCl and licocaine HCl. Exemplary beta-blockers include for example propranolol HCl. Exemplary 5-$HT_3$ receptor antagonists include for example ganisetron HCl, tropisetron HCl and ondansetron HCl. Exemplary anti-inflammatories include for example benzydamine HCl. Exemplary addiction weaning agents that can be used with the dosage form include for example nicotine, naltrexone (alcohol, opiate dependency) and lobeline sulfate HCl (methamphetamine dependency), The non-ionized form of drug compounds are generally believed to have better transport properties through oral mucosal membranes as compared to their ionized forms. It is indeed now well-known that non-ionized form of nicotine permeates at much higher rate as compared to ionized nicotine. Increasing pH increases the non-ionized fraction of nicotine, and increases its absorption via oral cavity and physiological effects. The dosage form can use a buffering agent (such as sodium bicarbonate) to convert to non-ionized or to ionized form, or to alter the ratio between the forms. It should be noted that where the discussion herein refers to the salt form of a titratable bioactive agent as an exemplary agent, the non-salt form can be used in the dosage form, and visa-versa (unless stability issues intervene). Salts are generally pharmaceutically acceptable salts.

Carboxylic acid-containing polymers can be used to form complexes with cationic forms of bioactive agents, which complexes can retard the release of bioactive agent. The molar amount of bioactive agent, and the molar amount of carboxylic acid moieties can be adjusted in view of the amount of such retardation sought. This methodology can be especially useful for bioactive agents that are highly water soluble (e.g., benzydamine HCl and naltrexone HCl). Carboxymethylcellulose and Carbopol are such polymers. Other appropriate polymers include for example anionic polymers of methacrylic acid and methacrylates with a —COOH group (e.g. Eudragit® L 100-55, supplied by Evonik).

Drug release with the dosage form is believed to be governed by two notable factors: polymer matrix erosion and drug solubility. Where the bioactive is sufficiently soluble that matrix erosion cannot be used as a sufficient release rate controller, complex formation as described here can be used to adjust release.

Carbopol, for example, is a weakly acidic polymer. At basic pH, carboxylic acid groups of Carbopol ionize. Basic drugs undergo complexation with anionic Carbopol when both drug and Carbopol are ionized. In most cases, the drug-Carbopol complex has less solubility than the pure drug. In practice, the common way of preparation of drug-polymer complex is by mixing the two components in aqueous or alcoholic-aqueous solution, followed by a drying step to collect the complex solid powder. The drug-polymer complex powder will then use as raw material, along with other excipients, to formulate into final drug dosage form such as tablets etc. However, as will be described further below, a one-step formulation process, effecting the complexation in situ, can be used.

In certain embodiments, the invention provides a single film (no subfilms) that provides sustained release of 1.5 hours or more and 15 hours or less for certain bioactive agents having a titratable amine and (a) two or more aromatic ring or (b) one or more aromatic rings that (i) incorporate nitrogen, and/or (ii) are directly substituted with N or O of substituent groups. In certain embodiments, the aromatic rings are directly substituted with two or more N or O of substituent groups. In certain embodiments, the bioactive agent includes an alkyl amine as a titratable amine. The single film is as outlined for the sustained-release subfilm, but includes as predominantly hydrophilic bioadhesive polymer(s) a predominant amount of crosslinked polymers of acrylic acid. In certain embodiments, crosslinked polymers of acrylic acid comprise 51% or more, 55% or more, 60% or more, 65% or more, 70% or more, 75% or more, 80% or more, 85% or more, 90% or more, 95% or more, or 100% of the predominantly hydrophilic bioadhesive polymer(s). Exemplary bioactive agents include naltrexone, chlorphenamine, chlorpheniramine, papaverine, propcaine, lidocaine, propranolol, lobeline, and the like. Single films of this type have delivered unexpectedly sustained release.

In one embodiment, the dosage form (single or dual subfilm) is applied to the top of the tongue and adheres to the palate, for instance as soon as subject closes his or her mouth. The film is designed such that it disintegrates and dissolves upon administration and the drug is released for systemic absorption or local treatment. It is anticipated, for a number of bioactive agents, that a large percentage of the active will be absorbed in the oral cavity, and a small portion of the drug (e.g., about 10-15%) will be swallowed by the saliva flow through the throat, to the stomach. Of course, for the quick-release subfilm, it is anticipated the most bioactive will be swallowed.

In certain embodiments, the quick-release side of the dosage form can be picked up with a finger or tool, and the other side applied to mucosal tissue, where the stronger adhesiveness of the other side will draw the dosage form to the mucosal tissue. In some embodiments, it is the quick-release side of the dosage form that is laid on the tongue, such that the other side transfers to the palate.

It can be important to know which subfilm is on which side of the dosage form. The packaging can be marked, and sidedness tracked for the short period between opening the packaging and applying to the target mucosa. Or, one or both subfilm can include a pharmaceutically acceptable dye such that the different subfilms provide a distinctly different color, such as when the major surfaces of the subfilms are viewed. The color can be used to help inform the user of the preferred side for application to the tongue, such that the other side transfers to the palate.

The dosage form can for example be individually packaged in a moisture-resistant, sealed multi-laminated aluminized pouch. Or, each dosage form (unit dosage) can be packaged in each compartment of a blister pack.

Fabrication can be, for example, by the solvent-casting method, or by the hot-melt extrusion process. In many cases, the solvent-casting method is simple and flexible. Generally, solvent-based casting process for fabricating a film involves three basic steps: a) preparation of wet casting solution, b) casting of wet film, and c) drying of the film. There are generally three more steps for finishing of the device fabrication process: d) die-cutting of the film into individual unit-dose discs, e) de-lamination of thin-film discs from a casting liner, and f) pouching of the discs. The final thin-form discs can be individually packaged in single pouches as single unit doses.

One embodiment of the fabrication process is described herein. First the active ingredient, with the polymers, flavors, plasticizers, preservatives, buffering agents, stabilizers or coloring agents are mixed in an aqueous and/or alcoholic solution to form a homogenous casting solution with a solid content of 20-40% and a viscosity of 5,000-20,000 cps. The homogenous coating solution is uniformly coated onto a casting polyester release liner with predetermined thickness (e.g., 20-50 mil wet film thickness). The cast film is subsequently dried in a forced-air oven at 60-80° C., removing water and/or alcohol. The above steps can be repeated for an over-cast fabrication of the second subfilm. That is, the casting solution of the second film is cast on the dried film of the first subfilm. The again dried in the forced air oven, The dried film (now dual layer) is die-cut into desired shape and sizes (e.g., 2.3 cm×2.3 cm squares, which may have round-cornered edges) of dosage units. The die-cut discs are delaminated so that the casting release liners are removed and discarded; the neat discs are then pouched. Pouching material is a multi-laminate construction stock (e.g., paper/aluminum/polyethylene), and pouching is done on single unit dose per pouch basis. Pouching protects and preserves stability of the drug delivery system over its shelf life.

Where the bioactive is an appropriate amine and the polymers include carboxylic acids, it is believed that the release controlling complexes will form in the above process.

EXAMPLE 1

A single-layer nicotine dosage form of the following composition was made:

| Ingredient | Quantity, g |
|---|---|
| Ethanol | 103 |
| Cremophor RH-40 | 2.4 |
| Cocoa Powder | 0.45 |
| Menthol | 3.3 |
| Peppermint oil | 2.3 |
| Carbopol 971 | 18.6 |
| Nicotine | 5.0 |
| Sodium EDTA | 0.10 |
| Magnasweet 100 | 0.3 |
| Sodium Bicarbonate | 0.4 |
| Water | 78.1 |
| Kollicoat IR | 5.3 |
| Saccharin | 0.2 |

These components are processed as follows:

1. In a mixing vessel, add in the menthol and water. Place the vessel in heated water bath (about 60° C.), mix the contents until all components are dissolved.
2. Add in the ethanol, Cremophor, and Peppermint Oil. Mix for 10 min.
3. Add all solid powder. Mix for 1.5 hour.
4. Coat the solution from Step 3 onto a polyester release liner (MediRelease 2249, Mylan Technologies) using a coating applicator with clearance of 25 mil.
5. Dry the coating from Step 4 in a convection oven at 60° C. for 30 min.

6. Die-cut dried sheets into 2.3 cm×2.3 cm squares.
7. Pouch each squares in multi-laminated protective sheet.

EXAMPLE 2

Following the procedure of the specification, naltrexone HCl single-layer dosage forms were made.

EXAMPLE 3

Following the procedure of the specification, lobeline sulfate single-layer dosage forms were made.

EXAMPLE 4

Following the procedure of the specification, granisetron HCl single-layer dosage forms were made. This can, for example, be used to treat chemotherapy-Induced nausea and vomiting.

EXAMPLE 5

A single-layer dosage form with the composition given below, was fabricated according to the methodology described above in the specification. Important parameters for controlling drug dissolution/release include film thickness, polymer type, and plasticizer, among others. The dosage forms (fixed size of 2.3 cm×2.3 cm, film weight of 80 mg, containing 25 mg naltrexone HCl) had good structural integrity, adequate mucosal adhesion, and a moderated drug release profile.

| Ingredient | Function | Composition (wt) |
| --- | --- | --- |
| Carbopol 971 | Predominantly Hydrophilic Bioadhesive Polymer | 26.3% |
| Kollicoat IR | Highly Water Soluble Polymer | 14.9% |
| Naltrexone HCl | Active Ingredient | 20.1% |
| Brij 58 | Release Modifier/Plasticizer | 14.3% |
| PEG 400 | Plasticizer | 10.5% |
| PEG 4000 | Plasticizer | 8.8% |
| Peppermint Oil | Flavoring Agent | 1.8% |
| Saccharin | Flavoring Agent | 1.8% |
| Sodium EDTA | Chelating Agent | 0.3% |
| Sodium Bicarbonate | Buffering Agent | 1.4% |

Figure 1:
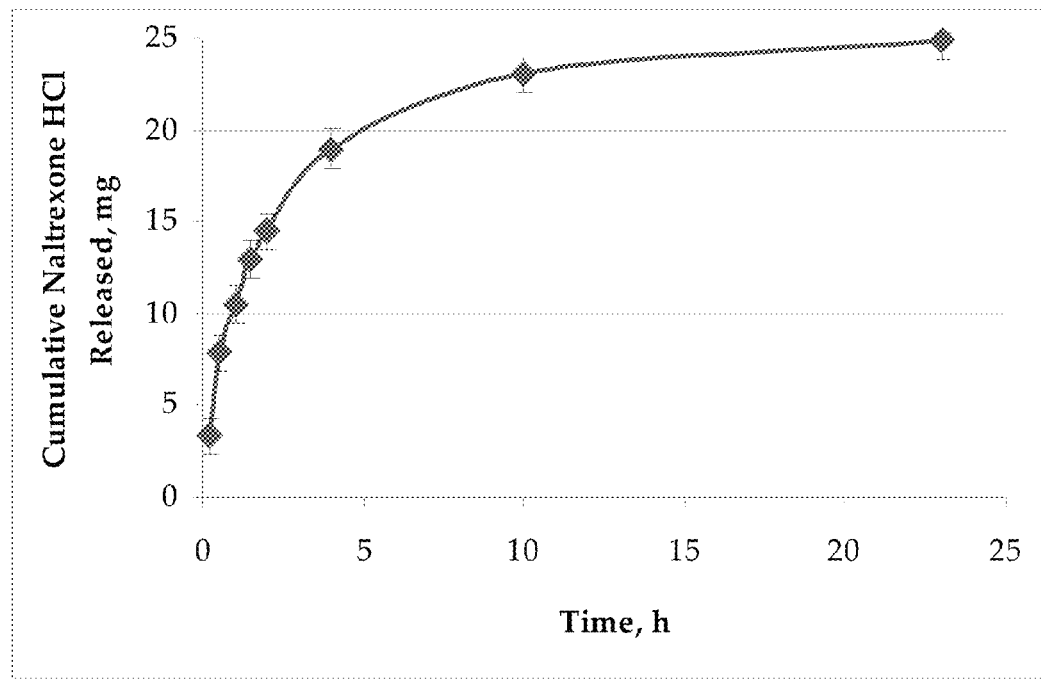

A drug release experiment was conducted, using USP phosphate buffer solution (pH 6.8) as the dissolution medium. Release of naltrexone HCl from the film, was determined by HPLC method as a function of time, and plotted in FIG. 1. FIG. 1 shows that about 50% of the naltrexone HCl was released within 1.5 h in near zero-order kinetics, and another 45% was released more slowly in the next 7 hours or so. Hence, the bioactive release period is approximately 8 h. The sustained drug release is believed to be due to both film composition and the formulation of drug-Carbopol complex. A bioactive agent release period of about 5 hours was obtained, and this period is anticipated to have been longer had the dosage form been adhered to an appropriate support.

EXAMPLE 6

Step A. Fast-dissolving Layer (FDL) Containing Nicotine

| The composition for forming this layer (quick release subfilm) is as follows: Ingredient | Quality, grams |
| --- | --- |
| Sodium EDTA | 0.18 |
| Magnasweet 100 | 0.46 |
| Sodium Bicarbonate | 0.79 |
| Carbopol 971 | 0.74 |
| Nicotine Polacrilex 20% USP | 6.35 |
| Mono-/Di-glycerides | 2.40 |
| Water | 114 |
| Kollicoat IR | 45.67 |
| Sodium Alginate Sodium | 1.38 |
| Sacharrin | 0.21 |
| Cremophor RH-40 | 4.86 |
| Cocoa Powder | 0.91 |
| Menthol | 4.59 |
| Peppermint oil | 1.83 |

The procedure for preparation was:

1. In a mixing vessel, add in menthol and water. Place the vessel in heated water bath (about 60° C.), mix the contents until all components are dissolved.
2. Add in mono-/diglycerides, Cremophor, and Peppermint Oil. Mix for 10 min.
3. Add all solid powder. Mix for 1.5 hour.
4. Coat the solution from Step 3 on polyester release liner, MediRelease 2249 (Mylan Technologies) using a coating applicator with clearance of 25 mil.
5. Dry the coating from Step 4 in a convection oven at 60° C. for 30 min.
6. The dried film sheet is ready to be over-coated with second layer.

Step B: Slow Release Layer (SRL) and Double-layer (DL) Containing Nicotine

The composition for forming this layer (quick release sub-film) is as follows:

| Ingredient | Quantity, g |
| --- | --- |
| Ethanol | 102.48 |
| Cremophor RH-40 | 2.43 |
| Cocoa Powder | 0.45 |
| Menthol | 2.30 |
| Peppermint oil | 0.96 |
| Mono/Diglycerides | 1.32 |
| Carbopol 971 | 18.58 |
| Nicotine Polacrilex 20% USP | 10.01 |
| Sodium EDTA | 0.10 |
| Magnasweet 100 | 0.23 |
| Sodium Bicarbonate | 0.40 |
| Water | 78.13 |
| Kollicoat IR | 5.32 |
| Sacharrin | 0.12 |

The procedure for preparation was:

1. In a mixing vessel, add in menthol, and water. Place the vessel in heated water bath (about 60° C.), mix the contents until all components are dissolved.
2. Add in ethanol, mono-/diglycerides, Cremophor, and Peppermint Oil. Mix for 10 min.
3. Add all solid powder. Mix for 1.5 hour. Coat a single layer to get samples of SRL film.
4. Overcoat solution from 3 onto the dried film sheet from Step A.

-continued

5. Dry the coating in a convection oven at 60° C. for 30 min.
6. Die-cut the dried sheet into 2.3 cm × 2.3 cm squares.
7. Test the preparations for assay contents and drug dissolution.

Nicotine content assays and the drug release assays were based on USP Monograph, using the HPLC (high performance chromatography) method. In vitro drug release tests were conducted in an incubator shaker in 100 mL of USP phosphate buffer, pH 6.8, at 37° C. and 100 rpm. Dissolution samples of 1 mL will be collected at pre-determined time points, and analyzed for nicotine assay. Nicotine content was:

FDL=1.5 mg nicotine/unit
SRL=3.0 mg nicotine/unit
DL=5.0 mg nicotine/unit

Dissolution results are presented in FIG. 2. The results show that the bilayer film releases the drug, nicotine, in the manner as anticipated. That is, in the bilayer film, the FDL component rapidly released 1.5 mg of nicotine in about 15 min, and the SRL component released nicotine slowly for period of up to about 150 min.

In this experiment, one side of the dosage form was not adhered to a non-eroding substrate. As such, the result may somewhat underestimate the sustained release expected when the dosage form is adhered to a surface such as the palate. However, the experiment is believed to provide a useful surrogate for one-sided erosion.

EXAMPLE 7

Similarly, dual-layer films containing naltrexone hydrochloride (HCl) were prepared. These preparations can be used for alcohol dependence treatments. The following preparations were prepared:

FDL=10 mg naltrexone HCl
SRL=15 mg naltrexone HCl
DL=25 mg naltrexone HCl

EXAMPLE 8

Similarly, dual-layer films containing lobeline sulfate were prepared. These preparations can be used for methamphetamine dependence (drug abuse) therapy.

The following preparations were prepared:

FDL=2.5 mg lobeline
SRL=5.0 mg lobeline
DL=7.5 mg lobeline

While the foregoing is directed to embodiments of the present invention, other and further embodiments of the invention may be devised without departing from the basic scope thereof, and the scope thereof is determined by the claims that follow. Any claim below that is written as dependent on an independent claim can also be written as dependent on any of the claims under such independent claim, except where logic forecloses such a dependency.

What is claimed is:

1. A dual-release, dual-adhesiveness flexible thin film dosage form comprising:
a mucoadhesive, planar quick-release subfilm comprising an admixture of polymers, which comprises (a) highly water-soluble polymer(s), (b) predominantly hydrophilic, bioadhesive polymer(s) and, uniformly distributed in the quick-release subfilm polymers, (c) a bioactive agent that is nicotine, naltrexone, lobeline or ondansetron, the polymers and other components of the quick-release subfilm adapted to provide 1 minute or more and 20 minutes or less erodibility for the quick-release subfilm; and
laminated against the quick-release subfilm, a mucoadhesive, planar sustained-release subfilm comprising an admixture of polymers, which comprises (i) predominantly hydrophilic, bioadhesive polymer(s), and, uniformly distributed in the sustained-release subfilm polymers, (ii) the bioactive agent, the polymers and other components of the sustained-release subfilm adapted to provide erodibility of 1 hour or more and 20 hours or less for the sustained-release subfilm, wherein both subfilms comprise (1) flavoring agent or agents and sweetener or sweeteners, (2) polyoxyethylenated castor oil derivative or derivatives and (3) di-glyceride or di-glycerides,
the dosage form having a thickness of 30 mil or less, and being more adhesive on the sustained-release side, the dosage form having no additional layers, and wherein the dosage for is individually packaged in a moisture-resistant compartment.

2. The thin film dosage form of claim 1, wherein the highly water-soluble polymers comprise soluble cellulose derivatives, polyvinylpyrrolidone, polyvinyl alcohol, polyethylene oxide, polyvinyl alcohol grafted polyethylene glycol copolymer, or mixtures thereof.

3. The thin film dosage form of claim 2, wherein the highly water-soluble polymers comprise soluble polyethylene oxide, polyvinyl alcohol grafted polyethylene glycol copolymer, or mixtures thereof.

4. The thin film dosage form of claim 1, wherein the predominantly hydrophilic, bioadhesive polymers comprise xanthan gum, carrageenan, pectin, sodium carboxymethylcellulose, alginate, polyacrylic acids, high molecular weight polyethylene oxide, or mixtures thereof.

5. The thin film dosage form of claim 4, wherein the predominantly hydrophilic, bioadhesive polymers comprise polyacrylic acids, high molecular weight polyethylene oxide, or mixtures thereof.

6. The thin film dosage form of claim 1, wherein the polymers and other components of the quick-release subfilm are adapted to provide 15 minutes or less erodibility for the quick-release subfilm.

7. The thin film dosage form of claim 1, wherein the polymers and other components of the sustained-release subfilm are adapted to provide a bioactive agent release period of 2 hours or more and 20 hours or less for the bioactive agent provided by the sustained-release subfilm.

8. A method of delivering a bioactive agent comprising applying the sustained-release subfilm of the thin film dosage form of claim 1 to mucosal tissue.

9. The method of claim 8, wherein the thin film dosage form is applied to mucosal tissue of the mouth.

10. The method of claim 9, wherein the quick-release subfilm of the thin film dosage form is applied to the top of the tongue, and the thin film dosage form is applied by transfer from the tongue to the palate.

11. The method of claim 8, further comprising providing the thin film dosage form so that the quick-release and the sustained release subfilms have distinct colors, applying the quick-release colored subfilm to a transfer intermediate, and then transferring the thin film dosage form to the mucosal tissue.

12. The thin film dosage form of claim 2, wherein the predominantly hydrophilic, bioadhesive polymers comprise xanthan gum, carrageenan, pectin, sodium carboxymethylcellulose, alginate, polyacrylic acids, high molecular weight polyethylene oxide, or mixtures thereof.

13. The thin film dosage form of claim 3, wherein the predominantly hydrophilic, bioadhesive polymers comprise xanthan gum, carrageenan, pectin, sodium carboxymethylcellulose, alginate, polyacrylic acids, high molecular weight polyethylene oxide, or mixtures thereof.

14. The thin film dosage form of claim 1, wherein both subfilms comprise mono-glyceride.

15. The thin film dosage form of claim 1, wherein the bioactive agent is nicotine.

16. The thin film dosage form of claim 1, wherein the bioactive agent is naltrexone.

17. The thin film dosage form of claim 1, wherein the bioactive agent is lobeline.

18. The thin film dosage form of claim 1, wherein the bioactive agent is ondansetron.

* * * * *